United States Patent [19]

Gribble et al.

[11] Patent Number: 5,447,954
[45] Date of Patent: Sep. 5, 1995

[54] PHENYLDERIVATE AS INHIBITORS OF ATP CITRATE LYASE

[75] Inventors: Andrew D. Gribble, Knebworth; Pieter H. E. Groot, Letchworth; Antony N. Shaw, Stevenage, all of England; Roland E. Dolle, King of Prussia, Pa.

[73] Assignee: SmithKline Beecham p.l.c., England

[21] Appl. No.: 331,613

[22] PCT Filed: May 5, 1992

[86] PCT No.: PCT/EP93/01071

§ 371 Date: Nov. 4, 1994

§ 102(e) Date: Nov. 4, 1994

[87] PCT Pub. No.: WO93/22304

PCT Pub. Date: Nov. 11, 1993

[30] Foreign Application Priority Data

May 5, 1992 [GB] United Kingdom .................. 9209628

[51] Int. Cl.⁶ .............................................. A61K 31/34
[52] U.S. Cl. ..................... 514/473; 514/570; 549/295; 549/313; 562/470
[58] Field of Search .............. 549/295, 313; 514/473, 514/570; 562/420

[56] References Cited

U.S. PATENT DOCUMENTS 3,248,187 4/1966 Bell ........................................ 44/349
3,261,782 7/1966 Anderson et al. ..................... 252/57

FOREIGN PATENT DOCUMENTS

0478147A1 4/1992 European Pat. Off. .
3813806A1 11/1989 Germany .

OTHER PUBLICATIONS

Journal of Medicinal Chemistry, vol. 25, No. 6, Jun. 1982.

*Primary Examiner*—C. Warren Ivy
*Assistant Examiner*—Amelia Owens
*Attorney, Agent, or Firm*—Wayne J. Dustman; Stephen Venetianer; Edward T. Lentz

[57] ABSTRACT

Compounds of the formula

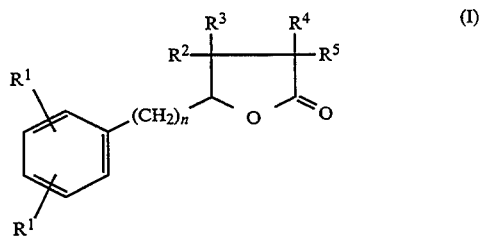

where the substituents are defined in the specification useful in the treatment of hyperlipidemia.

10 Claims, No Drawings

PHENYLDERIVATE AS INHIBITORS OF ATP CITRATE LYASE

This application is a 371 of PCT/EP93/01071 filed Apr. 29, 1993.

The present invention relates to certain novel compounds, processes and intermediates used in their preparation, pharmaceutical compositions containing them and their use in therapy.

It is now widely accepted that treatment of even moderate type II hypercholesterolaemia results in a reduction in mortality and morbidity due to coronary heart disease (CHD). Increased plasma concentrations of low density lipoprotein (LDL), the hallmark of type II hypercholesterolaemia are due to a variety of genetic and environmental factors resulting in increased LDL synthesis, decreased LDL catabolism or combinations of both. Current therapies for treatment of hypercholesterolaemia are directed towards stimulation of LDL catabolism (bile acid sequestrants and HMGCoA reductase inhibitors) as well as inhibition of LDL synthesis (nicotinic acid and maxepa fish oil).

The present invention relates to a new class of compounds which are expected to be of use in the treatment of hyperlipidaemia and preventing the development of consequent disorders like atherosclerosis and pancreatitis, as well as treatment of metabolic disorders like obesity. The compounds act by inhibition of the enzyme ATP citrate lyase, so inhibiting cholesterol synthesis and fatty acid synthesis resulting in lowered plasma cholesterol and triglyceride levels. In particular, it is expected that the compounds will be particularly useful in the treatment of mixed hyperlipidaemia (type IIb).

The present invention therefore provides, in a first aspect, compounds of structure (I):

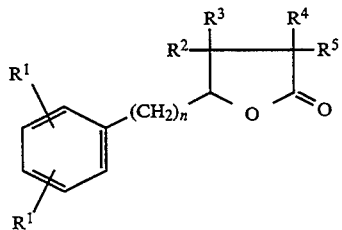

in which,
each group $R^1$ is independently a lipophilic and/or electron withdrawing group;
n is 5 to 8; and
either $R^2$ and $R^3$ are both hydrogen, $R^4$ is hydrogen or hydroxy and $R^5$ is $CH(R^6)R^7$ in which $R^6$ is hydrogen or hydroxy and $R^7$ is a carboxyl group or a carboxylic acid ester group hydrolysable to a carboxyl group; or $R^4$ is hydrogen and $R^5$ is hydrogen or hydroxy, $R^2$ is hydroxy and $R^3$ is a carboxyl group or a carboxylic acid ester group hydrolysable to a carboxyl group; or $R^2$ and $R^3$ are hydrogen and $R^4$ and $R^5$ together form a group $=C(R^6)R^7$ in which $R^6$ and $R^7$ are as defined above,
and salts thereof.

The term "lipophilic and/or electron withdrawing group" refers to groups such as halogen, in particular chlorine, nitro, cyano, $C_{1-4}$alkanoyl, optionally substituted phenyl$C_{1-4}$alkanoyl and fluorinated $C_{1-4}$alkyl such as trifluoromethyl. Other examples of such groups will be apparent to those skilled in the art. Suitable $C_{1-4}$alkanoyl groups include $CH_3CO-$ and $C_3H_7CO-$. Suitable phenyl$C_{1-4}$alkanoyl groups include, for example, phenylCO-(benzoyl).

"Carboxylic acid ester groups hydrolysable to a carboxyl group" as defined for $R^3$ and $R^7$ include, for example, groups of formula $C_2R^8$ in which $R^8$ is $C_{1-6}$alkyl, benzyl, acetoxymethyl and pivaloyloxymethyl; preferably $C_{1-6}$alkyl such as methyl. Other examples of such groups will be apparent to those skilled in the art.

Suitably, each group $R^1$ is independently a lipophilic and/or electron withdrawing group. Preferably each group $R^1$ is the same and positioned in the 2,3- or 2,4-positions of the ring, in particular the 2,4-positions. More preferably each group $R^1$ is the same and is halogen, in particular chlorine in the 2,4-positions of the ring.

Suitably, n is 5 to 8, preferably 6 or 7.

Suitably, $R^2$ and $R^3$ are both hydrogen, $R^4$ is hydrogen or hydroxy and $R^5$ is $CH(R^6)R^7$ in which $R^6$ is hydrogen or hydroxy and $R^7$ is a carboxyl group or a carboxylic acid ester group hydrolysable to a carboxyl group; or $R^4$ is hydrogen and $R^5$ is hydrogen or hydroxy, $R^2$ is hydroxy and $R^3$ is a carboxyl group or a carboxylic acid ester group hydrolysable to a carboxyl group; or $R^2$ and $R^3$ are hydrogen and $R^4$ and $R^5$ together form a group $=C(R^6)R^7$ in which $R^6$ and $R^7$ are as defined above.

Preferably, $R^2$ and $R^3$ are both hydrogen, $R^4$ is hydroxy and $R^5$ is $CH(R^6)R^7$ in which $R^6$ is hydrogen and $R^7$ is a carboxyl group.

Suitable salts of the compounds of structure (I) include, for example, basic salts, those formed by reaction with an appropriate base. Such salts include, for example, the sodium and potassium salts which can be prepared by methods well known to those skilled in the art, for example, the sodium salts can be formed by reaction with sodium hydroxide in an aqueous or non-aqueous medium.

The compounds of structure (I) can be prepared by procedures analogous to those known in the art. In a further aspect, there is therefore provided a process for preparing a compound of structure (I) which comprises:

(a) for compounds of structure (I) in which $R^2$ and $R^3$ are both hydrogen, $R^4$ is hydrogen or hydroxy and $R^5$ is $CH(R^6)R^7$, lactonisation of a compound of structure (II):

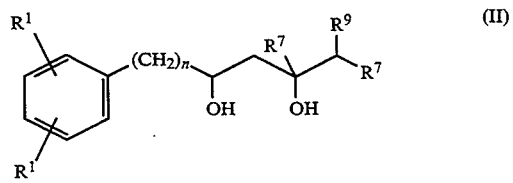

in which $R^1$, $R^7$ and n are as described for structure (I), and $R^9$ is hydrogen or $OR^{10}$ where $R^{10}$ is hydrogen or $C_{1-4}$alkyl, or (b) for compounds of structure (I) in which $R^4$ is hydrogen, $R^5$ is hydrogen or hydroxy, $R^2$ is hydroxy and $R^3$ is $CO_2H$ or a group hydrolysable to $CO_2H$, lactonisation of a compound of structure (III):

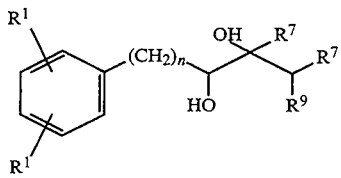 (III)

in which $R^1$, $R^7$ and n are as described for structure (I), and $R^9$ is hydrogen or $OR^{10}$ where $R^{10}$ is hydrogen or $C_{1-4}$alkyl as defined above, or (c) for compounds in which $R^2$ and $R^3$ are hydrogen, and $R^4$ and $R^5$ together form a group $=CR^6R^7$ in which $R^6$ and $R^7$ are as described for structure (I), lactonisation of a compound of structure (IV):

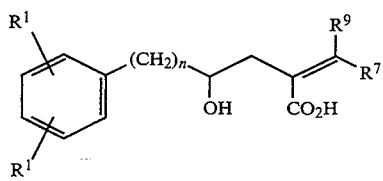 (IV)

in which $R^1$, $R^7$ and n are as described for structure (I), and $R^9$ is hydrogen or $OR^{10}$ where $R^{10}$ is hydrogen or $C_{1-4}$alkyl, and optionally thereafter,
  removing any protecting groups
  forming a salt.

The lactonisation of a compound of structure (II) can be carried out in a suitable solvent in the presence of an acid catalyst at a temperature of between ambient, and the boiling point of the solvent used, for as long as is required for reaction to go to completion. For example, the reaction can be carried out in tetrahydrofuran, in the presence of aqueous hydrochloride acid at a temperature of about 60° C. until reaction is complete. Alternative solvent systems and suitable acids will be apparent to those skilled in the art, for example the reaction can be carried out in a non-aqueous solvent such as diethyl ether or tetrahydrofuran, in the presence of acid (for example sulphuric acid) impregnated silica gel as a catalyst.

The intermediate compounds of structure (II) can be prepared by reduction of compounds of structure (V):

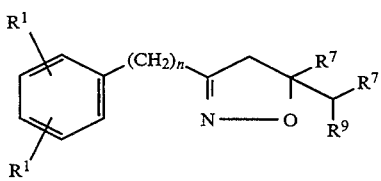 (V)

in which $R^1$, n, $R^7$ and $R^9$ are as described for structure (II). Suitable conditions for the reduction include hydrogenation over a suitable catalyst, in particular Raney nickel, in the presence of an acid such as hydroboric acid, in a suitable solvent such as a $C_{1-4}$alkanol, in particular methanol, followed by reduction of the resulting intermediate ketone with, for example, sodium borohydride in the presence of cerium chloride in a suitable solvent such as a $C_{1-4}$alkanol, in particular methanol or, preferably, sodium acetoxyborohydride (prepared in situ from sodium borohydride in acetic acid, or commercially available) in acetic acid as solvent.

The compounds of structure (V) can be prepared from compounds of structure (VI):

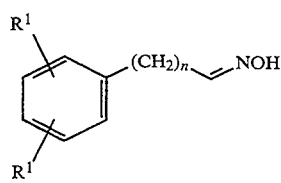 (VI)

in which $R^1$ and n are as described for structure (II), by reaction with a compound of structure (VII):

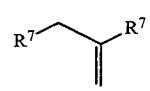 (VII)

in which $R^7$ is as described for structure (V). Suitable reaction conditions will be apparent to persons skilled in the art, for example, by reaction in a non-aqueous solvent, such as dichloromethane in the presence of aqueous sodium hypochlorite and triethylamine.

The compounds of structure (VI) can themselves be prepared from commercially available starting materials as described in the specific examples herein.

Alternatively, the compounds of structure (II) can be prepared by reduction of the compounds of structure (VIII):

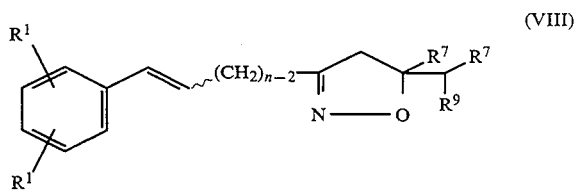 (VIII)

in which $R^1$, n, $R^7$ and $R^9$ are as described for structure (II). Suitable conditions include, for example, hydrogenation over a suitable catalyst, in particular Raney nickel, in the presence of an acid such as hydroboric acid, in a suitable solvent such as a $C_{1-4}$alkanol, in particular methanol, followed by hydrogenation over a noble metal catalyst such as platinum oxide, and then reduction of the intermediate ketone so formed with, for example, sodium borohydride in acetic acid.

Compounds of structure (VIII) can, themselves, be prepared by reaction of a compound of structure (IX):

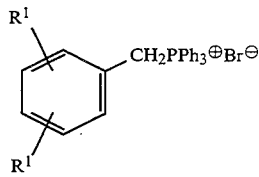 (IX)

in which $R^1$ is as described for structure (I), with a compound of structure (X):

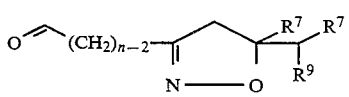 (X)

in which n, $R^7$ and $R^9$ are as described for structure (V).

Suitable reaction conditions will be apparent to those skilled in the art and include, for example, Wittig reaction conditions, using, for example, a suitable base such as sodium hydride, in a suitable solvent such as dimethyl sulphoxide, as hereinafter described. The compounds of structure (IX) can be prepared by standard procedures for the preparation of Wittig reagents. It will be appreciated by those skilled in the art that in the preparation of compounds of structure (I) in which at least one of the groups $R^1$ is an alkanoyl or optionally substituted phenylalkanoyl group, a keto protected form of the structure (IX) is used, that is to say, a compound of structure (IXA):

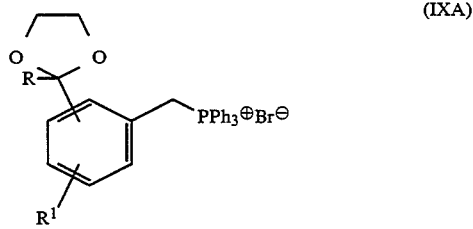
(IXA)

in which R is $C_{1-4}$alkyl or phenyl and $R^1$ is as described for structure (I).

Alternatively, the compounds of structure (VIII) can be prepared by reaction of a compound of structure (XI):

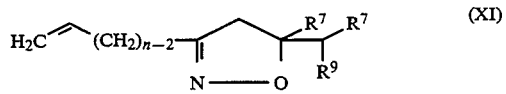
(XI)

in which n, $R^7$ and $R^9$ are as described for structure (II), with a compound of structure (XII):

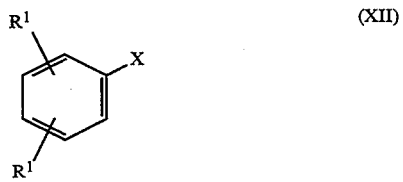
(XII)

in which $R^1$ is as described for structure (I) and X is halogen, in particular iodine.

The reaction between a compound of structure (XI) and a compound of structure (XII) can be carried out under Heck conditions as hereinafter described.

Compounds of structure (XI) can be prepared from compounds of structure (X) by reaction, for example, under Wittig conditions, using a suitable base such as sodium hydride, in a suitable solvent such as dimethyl sulphoxide as hereinafter described.

The compounds of structure (X) can be prepared from the compounds of structure (XIII):

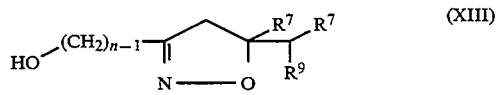
(XIII)

in which n, $R^7$ and $R^9$ are as described for structure (VI), under Swern oxidation conditions as hereinafter described.

Compounds of structure (XIII) can be prepared from the corresponding compounds of structure (XIV):

(XIV)

in which n is as described for structure (I) by reaction with a compound of structure (VII) as hereinbefore described for the reaction between a compound of structure (VI) and a compound of structure (VII). Compounds of structure (XIV) can be prepared by procedures known to those skilled in the art, for example the compound of structure (XIV) in which n is 6 can be prepared from $\epsilon$-caprolactone (commercially available) as hereinafter described.

The lactonisation of a compound of structure (III) can be carried out under standard conditions, for example as described above for the lactonisation of compounds of structure (II).

The intermediate compounds of structure (III) can themselves be prepared from compounds of structure (XV):

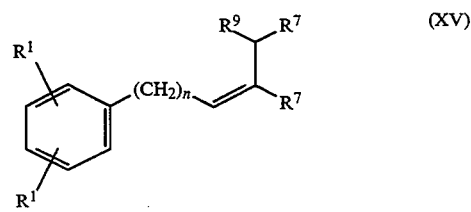
(XV)

in which $R^1$, n, $R^7$ and $R^9$ are as described for structure (III), by reaction, for example, with osmium tetroxide, N-methylmorpholine N-oxide in aqueous acetone as a solvent.

Alternatively, compounds of structure (III) can be prepared by ring-opening of an epoxide of formula (XVI):

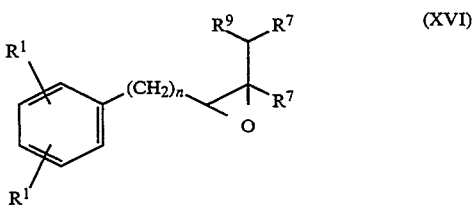
(XVI)

in which $R^1$, $R^2$, n, $R^7$ and $R^9$ are as described for structure (III).

The compounds of structure (XVI) can themselves be prepared by epoxidation of compounds of structure (XV) under standard conditions.

The compounds of structure (XV) can be prepared from compounds of structure (XVII):

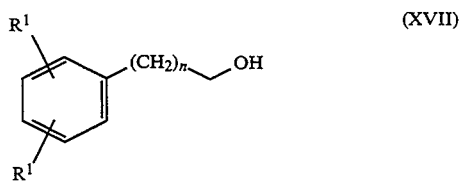
(XVII)

in which $R^1$ and n are as described for structure (XV) by, for example, oxidation under standard conditions, followed by reaction under Wittig conditions.

The compounds of structure (XVII) can be prepared from commercially available starting materials, using standard procedures as described herein in the specific examples.

Lactonisation of compounds of structure (IV) can be carried out under standard conditions as hereinbefore described for the lactonisation of the compounds of structure (II) and (III).

Compounds of structure (IV) can be prepared from the corresponding compounds of structure (XVIII):

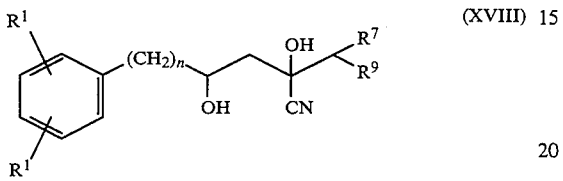

in which $R^1$, n, $R^7$ and $R^9$ are as described for structure (IV) by, for example, dehydration and hydrolysis using aqueous acid such as hydrochloric acid.

Compounds of structure (XVIII) can be prepared from the corresponding compounds of structure (XIX):

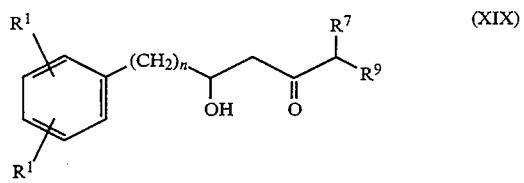

in which $R^1$, n, $R^7$ and $R^9$ are as described for structure (XVIII) by reaction, for example, with hydrogen cyanide.

Compounds of structure (XIX) can be prepared from compounds of structure (XX) and (XXI) under standard conditions as will be apparent to those skilled in the art.

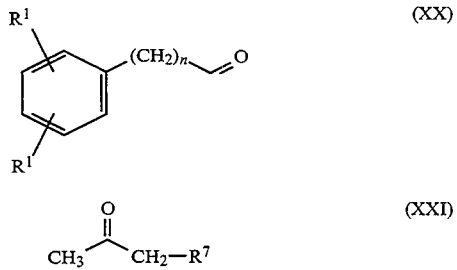

Compounds of structure (XX) and (XXI) are commercially available or can be prepared by standard techniques.

The intermediate compounds of structures (II), (III), (IV), (V), (VI), (VIII), (IX), (IXA), (X), (XI), (XIII), (XIV), (XV), (XVI), (XVII), (XVIII), (XIX) and (XX) are themselves novel and form a further aspect of the invention.

It will be appreciated that the compounds of structure (I) contain one or more asymmetric carbon atoms and are thus optically active compounds. As such, these compounds can exist as two (or more) optical isomers (enantiomers). Both the pure enantiomers, racemic mixtures (50% of each enantiomer thereof) and unequal mixtures of the two are included within the scope of the present invention. Further, all diastereomeric forms possible (pure enantiomers and mixtures thereof) are within the scope of the invention.

Pure enantiomers of the individual compounds claimed herein are obtained by resolution of mixtures using standard techniques, for example, via salt formation using, for example, D-(-)-threo-2-amino-1-(4-nitrophenyl)propan-1,3-diol as hereinafter described.

In addition, it will be apparent that the lactone form of structure (I) can also exist in the form of its open-chain equivalent of structure (IA) as follows:

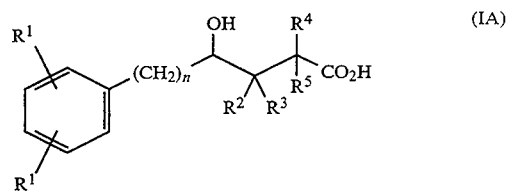

The present invention is intended to cover both of these forms in which $R^1$, n, $R^2$, $R^3$, $R^4$ and $R^5$ are as described for structure (I).

It will, of course, be appreciated that the lactone forms of structure (I) can be converted to the open chain forms (IA) under standard hydrolysis conditions.

Furthermore, it will be apparent that the compounds of structure (IA) in which $R^2$ and $R^3$ are both hydrogen, $R^4$ is hydrogen or hydroxy and $R^5$ is $CH(R^6)R^7$ in which $R^6$ is hydrogen or hydroxy and $R^7$ is a carboxyl group, can also exist in their corresponding 6-membered lactone ring form. Such 6-membered ring forms are also intended to be within the scope of the present invention.

Whilst the compounds of structure (I) are represented as lactone structures, it is believed that in vivo, that is to say on administration to subjects, the compounds convert to the open-chain form, and any carboxylic acid ester groups present convert to free carboxyl groups, and it is this open chain hydrolysed form in which the compounds bind to the ATP citrate lyase enzyme and exhibit the activity claimed herein. The active form of the compounds of structure (I) is therefore believed to be the structure (IB)

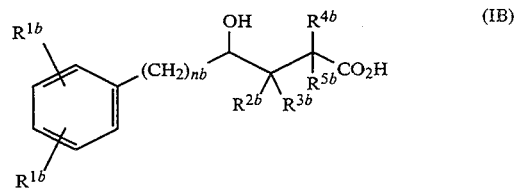

in which
each group $R^{1b}$ is independently a lipophilic and/or electron withdrawing group;
$n^b$ is 5 to 8; and
either $R^{2b}$ and $R^{3b}$ are both hydrogen, $R^{4b}$ is hydrogen or hydroxy and $R^{5b}$ is $CH(R^{6b})CO_2H$ in which $R^{6b}$ is hydrogen or hydroxy; or $R^{4b}$ is hydrogen and $R^{5b}$ is hydrogen or hydroxy, $R^{2b}$ is hydroxy and $R^{3b}$ is $CO_2H$; or $R^{2b}$ and $R^{3b}$ are hydrogen and $R^{4b}$ and $R^{5b}$ together form a group $=C(R^{6b})CO_2H$, and pharmaceutically acceptable salts thereof.

The compounds of structure (IB) and the pharmaceutically acceptable salts thereof have been found to be inhibitors of the enzyme ATP citrate lyase and, as such, are expected to be of use in medicine in the treatment of elevated serum cholesterol and triglyceride levels in mammals, including humans. In a still further aspect, the present invention therefore provides inhibitors of the enzyme ATP citrate lyase for use in therapy, in particular for lowering serum triglyceride and cholesterol levels in the treatment of mixed hyperlipidaemia (type (II)b). More particularly, the present invention provides compounds of structure (IB) and their pharmaceutically acceptable salts, for use in therapy, in particular for lowering serum triglyceride and cholesterol levels in the treatment of mixed hyperlipidaemia (Type (II)b). In addition, the compounds, that is to say, inhibitors of ATP citrate lyase, in particular the compounds of structure (IB), are expected to exhibit a beneficial effect in preventing the development of consequent disorders like atherosclerosis and pancreatitis as well as the treatment of metabolic disorders like obesity.

In therapeutic use, the compounds of the present invention are usually administered in a standard pharmaceutical composition. The present invention therefore provides, in a further aspect, pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example, syrups, suspensions or emulsions, tablets, capsules and lozenges.

A liquid formulation will generally consist of a suspension or solution of the compound or pharmaceutically acceptable salt in a suitable liquid carrier(s), for example, ethanol, glycerine, non-aqueous solvent, for example, polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carrier and then filled into a hard gelatin capsule; alternatively, a dispersion or suspension can be prepared using any suitable pharmaceutical carrier(s), for example, aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example, polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I), or a pharmaceutically acceptable salt thereof, which is active when administered in this way, with a binding and/or lubricating agent such as polymeric glycols, gelatins or cocoa butter or other low melting vegetable or synthetic waxes or fats.

Preferably, the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of lowering serum triglyceride and cholesterol levels which comprises administering to a mammal in need thereof an effective amount of an inhibitor of the enzyme ATP citrate lyase; and a method of lowering serum triglyceride and cholesterol levels which comprises administering to a subject in need thereof, an effective amount of a compound of structure (I) or (IB), or a pharmaceutically acceptable salt thereof.

The daily dosage regimen for an adult patient may be, for example, an oral dose of between 1 mg and 1000 mg, preferably between 0.1 mg and 250 mg, or an intravenous, subcutaneous, or intramuscular dose of between 0.1 mg and 100 mg, preferably between 0.1 mg and 25 mg, of the compound of formula (I) or a pharmaceutically acceptable salt thereof calculated as the free base, the compound being administered 1 to 4 times per day. Suitably, the compounds will be administered for a period of continuous therapy, for example, for a week or more.

In addition, the compounds of the present invention can be co-administered (together or sequentially) with further active ingredients, for example and other hypercholesterolaemic agents such as bile acid sequestrants, ACAT inhibitors and other drugs for the treatment of cardiovascular disease.

The following examples illustrate the invention. Temperatures are recorded in degrees centigrade.

EXAMPLE 1

±(3R*, 5S*)

3-Carboxy-11-(2,4-dichlorophenyl)-3,5-dihydroxyundecanoic acid, disodium salt (a) Methyl 7-(2,4-Dichlorophenyl)-6-heptenoate Sodium hydride (60% dispersion in oil, 14.8 g, 369.4 mmol) was washed with petroleum ether 40°-60° C., then heated to 80° C. in dimethyl sulphoxide (180 ml) under argon until gas evolution ceased. The solution was cooled to 0° C. in an ice-bath, and a solution of 5-carboxypentyltriphenylphosphonium bromide (82.4 g, 180.2 mmol) in dimethylsulphoxide (380 ml) was added. The solution was stirred for 0.5 h at room temperature, then cooled to 0° C. A solution of 2,4-dichlorobenzaldehyde (31.5 g, 180.2 mmol) in dimethylsulphoxide (80 ml) was added, and the mixture stirred at room temperature for 1 h, then poured into aqueous HCl. This mixture was extracted with ether. All extracts were washed with water, saturated aqueous NaCl and dried over MgSO$_4$. The solvent was removed under vacuum.

Concentrated H$_2$SO$_4$ (2 ml) was added to a solution of the residue in methanol (300 ml), and this was stirred at room temperature for 15 h. Saturated aqueous NaHCO$_3$ was added until pH neutral and solvent was removed under vacuum. The residue was partitioned between aqueous NaHCO$_3$ and ether. The ether layer was washed with aqueous HCl, water, saturated aqueous NaCl, and dried (MgSO$_4$). The solvent was removed under vacuum, the residue extracted with 10% ether/petroleum ether 40°-60° C., and the extracts filtered. The solvent was removed under vacuum, and the residue purified by chromatography on silica gel (10–30% ether/petroleum ether 40°–60° C.) to give the title compound (40.2 g) as an oil, comprising a mixture of E and Z isomers, which was used without further purification.

(b) 7-(2,4-Dichlorophenyl)-6-hepten-1-ol

Di-isobutylaluminium hydride (1.0M in dichloromethane, 308 ml, 308 mmol) was injected into a stirred solution of methyl 7-(2,4-dichlorophenyl)-6-heptenoate (40.2 g, 140 mmol) in dichloromethane (200 ml) at −78° C. under argon. After 5 min, the solution was warmed to 0° C., stirred for 0.5 h, then cooled again to −78° C. Water (102 ml) was injected slowly, while allowing the mixture to warm to room temperature. When solid had precipitated, ethyl acetate (400 ml) was added, then excess $NaHCO_3$, and the mixture stirred vigorously for 0.25 h. The solids were filtered off, the solvent removed under vacuum, and the residue purified by chromatography on silica gel (30–70% ether/petroleum ether 40°–60° C.) to give the title compound (31.7 g, 85%) as an oil, comprising a mixture of E and Z isomers.

(c) 7-(2,4-Dichlorophenyl)-1-heptanol

A solution of 7-(2,4-dichlorophenyl)-6-hepten-1-ol (31.7 g, 122 mmol) in methanol (150 ml) was shaken under hydrogen (50 psi) with platinum oxide (1.65 g, added in portions) until no starting material could be detected by NMR spectroscopy. The catalyst was filtered off, and the solvent removed under vacuum. The residue was dissolved in ether, and the solution filtered through a pad of silica gel. The solvent was removed under vacuum to give the title compound (30.5 g, 96%) as an oil.

(d) 7-(2,4-Dichlorophenyl) heptanaldoxime

Dimethylsulphoxide (15.2 ml, 214 mmol) was added slowly to a stirred solution of oxalyl chloride (9.35 ml, 107 mmol) in dichloromethane (150 ml) at −78° C. under argon. After 5 min, a solution of 7-(2,4-dichlorophenyl)-1-heptanol (20.0 g, 76.6 mmol) in dichloromethane (100 ml) was added by cannula. After stirring 0.5 h at −78° C., triethylamine (47 ml, 337 mmol) was injected. The mixture was stirred 5 min, allowed to warm to room temperature, then poured into 1M aqueous $NaHSO_4$. The product was extracted with ether. The extracts were washed with water, saturated aqueous NaCl, then the solvent removed under vacuum.

A solution of the crude aldehyde in ether (120 ml) was added to a stirred suspension of hydroxylamine hydrochloride (17.0 g, 245 mmol) in water (10 ml) at 0° C., followed by aqueous $Na_2CO_3$ (2.7M, 50 ml, 135 mmol). The mixture was stirred at room temperature for 2.5 h, poured into water, and extracted with ether. The extracts were washed with water, saturated aqueous NaCl, and dried ($MgSO_4$). The solvent was removed under vacuum, and the residue purified by chromatography on silica gel (30–50% ether/petroleum ether 40°–60° C.) to give the title compound (17.3 g, 82%) as a mixture of E and Z isomers.

(e) ±5-(Carbomethoxymethyl)-3-[6-(2, 4-dichlorophenyl)-hexyl]-5-methoxycarbonyl-4,5-dihydroisoxazole Aqueous NaOCl (2.0M, 340 ml, 680 mmol) and triethylamine (2.5 ml, 18.0 mmol) were added in 4 portions separately over 40 h to a stirred solution of 7-(2,4-dichlorophenyl)-heptanaldoxime (17.3 g, 63.1 mmol), and dimethyl itaconate (23.0 g, 145 mmol) in dichloromethane (200 ml). The mixture was stirred vigorously at room temperature over this period, then poured into water and extracted with ether. The extracts were washed with water, saturated aqueous NaCl, and dried ($MgSO_4$). The solvent was removed under vacuum, and the residue purified by chromatography on silica gel (30–60% ether/petroleum ether 40°–60° C.) to give the title compound (19.5 g, 72%) as an oil.

(f) ±Methyl 11-(2,4-dichlorophenyl)-3-hydroxy-3-methoxycarbonyl-5-oxo-undecanoate A solution of ±5-(carbomethoxymethyl)-3-[6-(2,4-dichlorophenyl)hexyl]-5-methoxycarbonyl-4,5-dihydroisoxazole (19.5 g, 45.3 mmol) and boric acid (8.39 g, 136 mmol) in methanol was shaken with Raney nickel (50% slurry in water, 8 g) under hydrogen (50 psi) at room temperature for 2 h. The catalyst was removed by filtration, and most of the solvent removed under vacuum. The mixture was diluted with water, and extracted with ethyl acetate. The extracts were washed with water, saturated aqueous NaCl, and dried ($MgSO_4$) . The solvent was removed under vacuum, and the residue purified by chromatography on silica gel (50–80% ether/petroleum ether 40°–60° C.) to give the title compound (16.7 g, 85%) as an oil.

(g) ±(3R*,5S*) 3-Carboxy-11-(2,4-dichlorophenyl)-3,5-dihydroxyundecanoic acid, disodium salt Sodium borohydride (1.47 g, 38.8) was added in portions to a stirred solution of ± methyl 11-(2,4-dichlorophenyl)-3-hydroxy-3-methoxycarbonyl-5-oxo-undecanoate (16.0 g, 36.9 mmol) and cerium (III) chloride heptahydrate (14.4 g, 38.8 mmol) in methanol (200 ml) at 0° C. The solution was stirred for 0.5 h, then quenched with aqueous HCl. The mixture was diluted with water, and extracted with ether. The extracts were washed with water, saturated aqueous NaCl, dried ($MgSO_4$), and the solvent removed under vacuum. Aqueous NaOH (1.5M, 100 ml, 150 mmol) was added to a stirred solution of the crude hydroxy ester in ethanol (100 ml) at 0° C. The mixture was stirred for 4 h, diluted with ethanol (200 ml), and filtered. The solid was recrystallised (aqueous ethanol) to give the title compound (11.9 g, a monohydrate, 69%) as a white solid, m.p. indeterminate.

$C_{18}H_{22}Cl_2O_6Na_2.H_2O$ Found C 46.03%, H 5.20% Requires C 46.07%, H 5.15%.

EXAMPLE 2

±(3R*, 5S*) 3-Carboxymethyl-5-[6-(2,4-dichlorophenyl)hexyl]3-hydroxytetrahydrofuran-2-one A mixture of ±(3R*, 5S*) 3-carboxy-11-(2,4-dichlorophenyl)-3,5-dihydroxyundecanoic acid, disodium salt (11.8 g, 25.1 mmol), aqueous HCl (3M, 200 ml), and tetrahydrofuran (200 ml) was heated at 60° C. for 6 h, then cooled. Most of the tetrahydrofuran was removed under vacuum. The residual mixture was diluted with water, and extracted with ether. The extracts were washed with water, saturated aqueous NaCl, and dried ($MgSO_4$). The solvent was removed under vacuum, and the residue recrystallised (ether/petroleum ether 40°–60° C.) to give the title compound (8.80 g, 90%) as a white solid, m.p. 77°–79° C.

$C_{18}H_{22}Cl_2O_5$ Found C 55.34%, H 5.64% Requires C 55.54%, H 5.70%.

EXAMPLE 3

±(E)-3-Carboxy-11-(2,4-dichlorophenyl)-5-hydroxy-2-undecenoic acid (a) ±Methyl 11-(2,4-dichlorophenyl)-5-hydroxy-3-oxoundecanoate Dimethylsulphoxide (0.381 ml, 5.36 mmol) was injected dropwise into a stirred solution of oxalyl chloride (0.234 ml, 2.68 mmol) in dichloromethane (4 ml) at −78° C. under argon. After 5 min, a solution of 7-(2,4-dichlorophenyl)-1-heptanol (see example 1, 500 mg, 1.91 mmol) in dichloromethane (4 ml) was added by cannula. The mixture was stirred for 0.5 h, then triethylamine (1.17 ml, 8.40 mmol) added. The reaction was allowed to warm to room temperature, then poured into aqueous NaHSO4. The mixture was extracted with ether, and the extracts washed with water, saturated aqueous NaCl, and dried (MgSO4). The solvent was removed under vacuum.

Methyl acetoacetate (0.247 ml, 2.29 mmol) was added dropwise to a stirred suspension of sodium hydride (61 mg, 2.52 mmol) in tetrahydrofuran (2 ml) at 0° C. under argon. The solution was stirred 0.5 h at room temperature, cooled to 0° C., and n-butyllithium (2.5M in hexanes, 1.01 ml, 2.52 mmol) injected. This solution was stirred 0.25 h at room temperature, cooled to −78° C., and a solution of the crude aldehyde in tetrahydrofuran (3 ml) added. The mixture was stirred for 0.3 h at −78° C., allowed to warm to room temperature, then poured into aqueous NaHSO4, and extracted with ether. The extracts were washed with water, saturated aqueous NaCl, and dried (MgSO4). The solvent was removed under vacuum, and the residue purified by chromatography on silica gel (60–100% ether/petroleum ether 40°–60° C.) to give the title compound (563 mg, 79%) as an oil.

(b) ±(E)-3-Carboxy-11-(2,4-dichlorophenyl)-5-hydroxy-2-undecenoic acid

Aqueous KH2PO4 (1.12M, 13 ml, 14.6 mmol) was added to a stirred mixture of ± methyl 11-(2,4-dichlorophenyl)-5-hydroxy-3-oxo-undecanoate (547 mg, 1.46 mmol), KCN (951 mg, 14.6 mmol), and ether (8 ml). The mixture was stirred vigorously for 18 h, then conc. aqueous HCl (1.25 ml, 14.6 mmol) added dropwise. The ether layer was removed, and the aqueous washed with ether. All extracts were concentrated under vacuum.

The crude cyanohydrin was heated under reflux in aqueous HCl (7.7M) for 3.5 h. The reaction was cooled, diluted with water, and the mixture extracted with ether. The extracts were concentrated under vacuum. Aqueous NaOH ( 1M, 4 ml ) was added to a stirred solution of the residue in ethanol (5 ml) at 0° C. After 1 h, the precipitate was filtered off, and the filtrate diluted with water. This solution was washed with ether, acidified to pH 1.5, and extracted with ether. The extracts were washed with water, saturated aqueous NaCl, and dried (MgSO4). The solvent was removed under vacuum, and the residue recrystallised (ether/petroleum ether 40°–60° C.) to give the title compound (110 mg, 19%) as a white solid, m.p. 92°–93° C.

$C_{18}H_{22}Cl_2O_5$ Found C 55.66%, H 5.72% Requires C 55.54%, H 5.70%.

EXAMPLE 4

±(3R*,5R*) 3-Carboxy-11-(2,4-dichlorophenyl)-3,5-dihydroxyundecanoic acid, disodium salt The precipitated sodium salts obtained during the preparation of the compound of example 3b were recrystallised (aqueous ethanol) to give a 1:1 mixture of the title compound and its diastereoisomer (131 mg, 19%) as a white solid, m.p. indeterminate.

$C_{18}H_{22}Cl_2O_6 \cdot Na_2 \cdot 1.3H_2O$ Found C 45.54%, H 5.07% Requires C 45.54%, H 5.23%.

EXAMPLE 5

±(4R*,5S*) 4-Carboxy-5-[8-(2,4-dichlorophenyl)octyl]-4-hydroxytetrahydrofuran-2-one (a) (E)-Methyl 12-(2,4-Dichlorophenyl)-3-methoxycarbonyl-3-dodecenoate Dimethylsulphoxide (1.37 ml, 19.3 mmol) was added dropwise to a stirred solution of oxalyl chloride (0.844 ml, 9.67 mmol) in dichloromethane (35 ml) at −78° C. under argon. After 5 min, a solution of 9-(2,4-dichlorophenyl)-1-nonanol (2.00 g, 6.91 mmol: prepared in analogous fashion to 7-(2,4-dichlorophenyl)-1-heptanol described in example 1) in dichloromethane (10 ml ) was added by cannula. After a further 0.5 h, triethylamine (4.24 ml, 30.4 mmol) was injected, and the reaction allowed to warm to room temperature. The mixture was poured into aqueous NaHSO4 and products extracted with ether. The extracts were washed with water, saturated aqueous NaCl, and dried (MgSO4). The solvent was removed under vacuum. A solution of the crude aldehyde and 1,2di(methoxycarbonyl)ethylenetriphenylphosphorane (4.21 g, 10.4 mmol) in toluene (25 ml) was heated at 100° C. for 24 h, then cooled. The solvent was removed under vacuum, and the residue purified by chromatography on silica gel (10–40% ether/petroleum ether 40°–60° C.) to give the title compound (2.46 g, 86%) as an oil.

(b) ±(3R*,4S*) Methyl 12-(2,4-Dichlorophenyl)-3,4-dihydroxy-3-methoxycarbonyldodecanoate A mixture of (E) methyl 12-(2,4-dichlorophenyl)-3-methoxycarbonyl-3-dodecenoate (1.50 g, 3.61 mmol), osmium tetroxide (0.229 ml of a 2% solution in t-butanol, 0.018 mmol), N-methylmorpholine-N-oxide (634 mg, 5.42 mmol), water (2 ml), and acetone (2 ml) was stirred at room temperature for 64 h. Aqueous NaHSO3 (1.1M, 6 ml) was added, and the mixture filtered, after 20 min, through a plug of silica gel. The silica gel plug was washed with ether, then the filtrate washed with aqueous HCl, water, and saturated aqueous NaCl. After drying (MgSO4), the solvent was removed under vacuum, and the residue purified by chromatography on silica gel (50–100% ether/petroleum ether 40°–60° C.) to give the title compound (1.33 g), contaminated with the 5-ring lactone.

(c) ±(4R*,5S*) 4-Carboxy-5-[8-(2,4-dichlorophenyl)octyl]-4-hydroxytetrahydrofuran-2-one ±(3R*,4S*) Methyl 12-(2,4-dichlorophenyl)-3,4-dihydroxy-3-methoxycarbonyl-3-dodecanoate (0.95 g, 2.11 mmol) was heated under reflux in aqueous HCl (7.7M) for 3.5 h. The mixture was cooled, diluted with water, and extracted with ether. The extracts were washed with aqueous NaOH, then the aqueous extracts washed with ether, acidified (aqueous HCl), and extracted again with ether. The extracts were washed with water, saturated aqueous NaCl, and dried (MgSO$_4$). The solvent was removed under vacuum. The crude diacid was stirred in ether with silica gel (5 g) impregnated with 0.5 ml 2M aqueous H$_2$SO$_4$ at room temperature for 18 h, then the mixture filtered, and the solvent removed under vacuum from the filtrate. The residue was recrystallised (dichloromethane/petroleum ether 40°–60° C.) to give the title compound (485 mg, 57%) as a gummy solid.

C$_{19}$H$_{24}$Cl$_2$O$_5$ Found C 56.55%, H 6.04% Requires C 56.59%, H 6.00%.

EXAMPLE 6

±(3R*,4S*) 3-Carboxy-11-(2 4-dichlorophenyl)-3 4-dihydroxyundecanoic acid

±(3R*,4S*) Methyl 11-(2,4-dichlorophenyl)-3,4-dihydroxy-3-methoxycarbonylundecanoate (189 mg, 0.434 mmol: prepared in analogous fashion to the higher homologue described in example 5) was heated under reflux in aqueous HCl (7.7M) for 3 h. The solution was cooled, diluted with water, and extracted with ether. The extracts were washed with aqueous NaOH, then the aqueous phase washed with ether, and acidified (aqueous HCl). The mixture was extracted with ether again. The extracts were washed with water, saturated aqueous NaCl, and dried (MgSO$_4$). The solvent was removed under vacuum, and the residue recrystallised (ether/petroleum ether 40°–60° C.) to give the title compound (115 mg, 68%) as a white solid, m.p. 104°–105° C.

C$_{18}$H$_{24}$Cl$_2$O$_6$ Found C 53.00%, H 5.93% Requires C 53.08%, H 5.94%.

EXAMPLE 7

±(4R*,5R*) 4-Carboxy-5-[8-(2,4-dichlorophenyl)octyl]-4-hydroxytetrahydrofuran-2-one a) ±(3R*,4S*) Methyl 12-(2,4-Dichlorophenyl)-3,4-epoxy-3-methoxycarbonyldodecanoate (E)-Methyl 12-(2,4-dichlorophenyl)-3-methoxycarbonyl-3-dodecenoate (686 mg, 1.65 mmol, described in example 4) and 3-chloroperbenzoic acid (5.7 g of 55% grade, 18.2 mmol) were heated under reflux in dichloromethane (15 ml) for 24 h. The mixture was cooled and poured into aqueous NaHCO$_3$/Na$_2$SO$_3$. This mixture was stirred for 10 min, then extracted with dichloromethane. The extracts were washed with aqueous NaHC$_3$, water, saturated aqueous NaCl, and dried (MgSO$_4$). The solvent was removed under vacuum, and the residue purified by chromatography on silica gel (20–40% ether/petroleum ether 40–60%) to give the title compound (369 mg, 52%) as an oil.

b) ±(4R*,5R*,) 5-[8-(2,4-Dichlorophenyl)octyl]-4-hydroxy-4-methoxycarbonyltetrahydrofuran-2-one ±(3R*,4S*) Methyl 12-(2,4-dichlorophenyl)-3,4-epoxy-3-methoxycarbonyldodecanoate (314 mg, 0.728 mmol) was heated at reflux in aqueous H$_2$SO$_4$ (7.5M) for 3.5 h. The solution was diluted with water, and extracted with ether. The extracts were washed with water, saturated aqueous NaCl, and dried (MgSO$_4$). The solvent was removed under vacuum. Diazomethane, generated from diazald (450 mg, 2.10 mmol) and aqueous KOH (10.7M), was passed in a stream of ether saturated nitrogen through a solution of the crude acid in 10% methanol/ether (10 ml) until a yellow colouration was seen in the reaction flask. Excess diazomethane was quenched with acetic acid, then the solvent removed under vacuum. The residue was purified by chromatography on silica gel (50–80% ether/petroleum ether 40°–60° C.) to give the title compound (198 mg, 65%) as an oil.

(c) ±(4R*,5R*) 4-Carboxy-5-[8-(2,4-dichlorophenyl)octyl]-4-hydroxytetrahydrofuran-2-one Aqueous NaOH (1M, 4 ml, 4.0 mmol) was added dropwise to a stirred solution of ±(4R*,5R*,) 5-[8-(2,4-dichlorophenyl)-octyl]-4-hydroxy-4-methoxycarbonyltetrahydrofuran-2-one (198 mg, 0.474 mmol) in methanol (4 ml) at 0° C. The solution was stirred at room temperature for 24 h, diluted with water, and washed with ether. The aqueous phase was acidified (aqueous HCl), and extracted with ether. The extracts were washed with water, saturated aqueous NaCl, and dried (MgSO$_4$). The solvent was removed under vacuum. The crude diacid was stirred with silica gel (3 g), impregnated with 2M aqueous H$_2$SO$_4$ (0.15 ml), in ether for 1 h. The mixture was filtered, and the solvent removed from the filtrate under vacuum to give the title compound (107 mg), (δ 200 MHz, CDCl$_3$) 7.34–7.10 (3H, m), 4.66 (1H, dd), 3.25 (1H, d), 2.77 (1H, d), 2.67 (2H, t), 1.95–1.20 (14H, m), contaminated with a small amount of ±(E) (4R*,5R*) 4-carboxy-5-[8-(2,4-dichlorophenyl)-7-octenyl]-4-hydroxytetrahydrofuran-2-one.

EXAMPLE 8

±(2R*,3R*,5S*) 3-Carboxy-11-(2,4-dichlorophenyl)-2,3,5-trihydroxyundecanoic acid, disodium salt (a) ±(3R*,5S*) 3-Carbomethoxymethyl-5-[6-(2,4dichlorophenyl)hexyl]-3-hydroxytetrahydrofuran-2-one Diazomethane, generated from diazald (1.37 g, 6.38 mmol) and 60% aqueous KOH (6 ml) in carbitol (6 ml) and ether (6 ml), was bubbled in a stream of ether saturated nitrogen through a solution of ±(3R*,5S*) 3-carboxymethyl-5-[6-(2,4-dichloro-phenyl)hexyl]-3-hydroxytetrahydrofuran-2-one (1.24 g, 3.19 mmol, see example 2) in 10% methanol/ether (12 ml). When a yellow colour appeared in the solution, the excess diazomethane was quenched with acetic acid, then the solvent removed under vacuum. The residue was purified by chromatography on silica gel (50–100% ether/petroleum ether 40°–60° C.) to give the title compound (1.15 g, 90%) as an oil.

(b) ±(1'R*,3R*,5S*) 3-[(Carbomethoxy)hydroxymethyl]-5-[6(2,4-dichlorophenyl)hexyl]-3-hydroxytetrahydrofuran-2-one n-Butyllithium (3.27 ml, 8.18 mmol, 2.5M in hexanes) was injected into a stirred solution of hexamethyldisilazane (1.73 ml, 8.18 mmol) in tetrahydrofuran (15 ml) at 0° C. under argon. After 5 min, the solution was cooled to −78° C. and a solution of ±(3R*, 5S*) 3-(carbomethoxymethyl)-5-[6-(2, 4dichlorophenyl)hexyl]-3-hydroxytetrahydrofuran-2-one (1.15 g, 2.85 mmol) in tetrahydrofuran (10 ml) was added by cannula slowly. After 1 h at −78° C., a solution of 2-(benzenesulphonyl)-3-phenyloxaziridine (1.07 g, 4.09 mmol) in tetrahydrofuran (7 ml) was added by cannula. The solution was stirred at −78° C. for 2 h, at −50° C. for 2.5 h, then allowed to warm to 0° C.

Aqueous HCl was added, and the mixture extracted with ether. The extracts were washed with water, saturated aqueous NaCl, and dried (MgSO$_4$). The solvent was removed under vacuum, and the residue purified by chromatography on silica gel (60–100% ether/petroleum ether 40°–60° C.) to give the title compound (236 mg, 20%) as an oil, as well as the (1'R*,3S*,5R*)-diastereoisomer (145mg, 12%), also as an oil.

(C) ±(2R*,3R*,5S*) 3-Carboxy-11-(2,4-dichlorophenyl)-2,3,5-trihydroxyundecanoic acid, disodium salt Aqueous NaOH (1M, 2.25 ml, 2.25 mmol) was added dropwise to a stirred solution of ±(1'R*,3R*,5S*) 3-[(carbomethoxy)-hydroxymethyl]-5-[6-(2,4-dichlorophenyl)hexyl]-3-hydroxytetrahydrofuran-2-one (235 mg, 0.56 mmol) in methanol (6 ml) at 0° C. The solution was stirred 10 min at 0° C., then 3 h at room temperature.

Methanol was removed under vacuum, the residue diluted with water, and acidified with aqueous HCl. The mixture was extracted with ether, and the extracts washed with water. The solvent was removed under vacuum, and the wet residue dissolved in ethanol (20 ml). Aqueous NaOH (1M, 1.4 ml, 1.4 mmol) was added. The mixture was allowed to stand for 45min, then boiled and cooled to 0° C. The solid was filtered off, washed with 5% water/ethanol and dried to give the title compound (181 mg, 69%), m.p. indeterminate, contaminated with 4% of the (2R*,3S*,5R*) diastereoisomer.

$C_{18}H_{22}Cl_2Na_2O_7$. $0.84H_2O$ Found C 44.76%, H 4.55%. Requires C 44.82%, H 4.95%.

EXAMPLE 9

±(2R*,3S*,5R*) 3-Carboxy-11-(2,4-dichlorophenyl)-2,3,5-trihydroxyundecanoic acid, disodium salt Aqueous NaOH (1M, 1.38 ml, 1.38 mmol) was added dropwise to a stirred solution of ±(1'R*,3S*,5R*) 3-[(carbomethoxy)-hydroxy-methyl]-5-[6-(2,4-dichlorophenyl)hexyl]-3-hydroxytetrahydrofuran-2-one (145 mg, 0.346 mmol) in methanol (4 ml) at 0° C. The solution was stirred at 0° C. for 10 min, then at room temperature for 3 h. Methanol was removed under vacuum, and the aqueous residue acidified with aqueous HCl. The mixture was extracted with ether, and the extracts washed with water. The solvent was removed under vacuum. The residue was dissolved in ethanol (15 ml), and the solution filtered. Aqueous NaOH (1M, 0.8 ml, 0.8 mmol) was added, the mixture allowed to stand for 45 min, then boiled and cooled to 0° C. The solid was filtered off, washed with 5% water/ethanol, and dried to give the title compound (111 mg, 69%), m.p. indeterminate, contaminated with 20% of the (2R*,3R*,5S*) diastereoisomer.

$C_{18}H_{22}Cl_2Na_2O_7 \cdot 0.9H_2O$ Found C 44.66%, H 4.57%. Requires C 44.72%, H 4.96%.

EXAMPLE 10

±(3R*,5R*) 3-(Carboxymethyl)-5-[6-(2,4-dichlorophenyl)hexyl]tetrahydrofuran-2-one and its diastereoisomer (a) 8-(2,4-Dichlorophenyl)-1-octene Dimethylsulphoxide (0.761 ml, 10.72 mmol) was added dropwise to a stirred solution of oxalyl chloride (0,468 ml, 5.36 mmol) in dichloromethane (10 ml) at −78° C. under argon. After 3 min, a solution of 7-(2,4-dichlorophenyl)-1-heptanol (1.00 g, 3.83 mmol, see example 1c) in dichloromethane (5 ml) was added by cannula. After a further 30 min, triethylamine (2.35 ml, 16.9 mmol) was injected and the mixture warmed to room temperature, poured into aqueous HCl, and extracted with ether. The extracts were washed with water, saturated aqueous NaCl, and dried (MgSO4). The solvent was removed under vacuum.

n-Butyllithium (2.5M, 3.37 ml, 8.43 mmol) was added to a stirred suspension of methyltriphenylphosphonium bromide (2.74 g, 7.66 mmol) in tetrahydrofuran (15 ml) at 0° C. under argon. The solution was stirred for 0.5 h, then cooled to −78° C. A solution of the crude aldehyde in tetrahydrofuran (5 ml) was added by cannula. After 5 min, the solution was warmed to room temperature, stirred for 1 h, then poured into aqueous HCl and extracted with ether. The extracts were washed with water, saturated aqueous NaCl, and dried (MgSO4). The solvent was removed under vacuum, and the residue triturated with 10% ether/petroleum ether 40°–60° C. The extracts were filtered through a plug of silica gel, and the filtrate concentrated under vacuum to give the title compound (697 mg), sufficiently pure to use in the next reaction.

(b) ±2-[6-(2,4-Dichlorophenyl)hexyl]oxirane m-Chloroperbenzoic acid (50% grade, 1.38 g, 4.01 mmol) was added in portions to a vigorously stirred mixture of 8-(2,4-dichlorophenyl)-1-octene (687 mg, 2.67 mmol), saturated aqueous NaHCO3 (15 ml), and dichloromethane (10 ml) at 0° C. The mixture was stirred for 5 min at 0° C., at room temperature for 1 h, then poured into water, and extracted with ether. The extracts were washed with aqueous Na2SO3/NaHCO3, water, saturated aqueous NaCl, and dried (MgSO4). The solvent was removed under vacuum and the residue purified by chromatography on silica gel (5–20% ether/petroleum ether 40°–60° C.) to give the title compound (265 mg, 25%, 3 steps) as an oil.

(c) ±(3R*,5R*) 3-(Carbomethoxymethyl)-5-[6-(2,4-dichlorophenyl)hexyl]tetrahydrofuran-2-one and its diastereoisomer.

n-Butyllithium (2.5M, 1.22 ml, 3.06 mmol) was added to a stirred solution of hexamethyldisilazane (0.646 ml, 3.06 mmol) in tetrahydrofuran (5 ml) at 0° C. under argon. The solution was stirred 5 min, then cooled to −78° C. A solution of diethyl succinate (0.462 ml, 2.78 mmol) in tetrahydrofuran (3 ml) was added slowly by cannula, and the mixture stirred for 30 min. A solution of ±2-[6-(2,4-dichlorophenyl)hexyl]oxiirane (253 mg, 0.926 mmol) in tetrahydrofuran (3 ml) was then added by cannula, followed immediately by boron trifluoride etherate (0.125 ml, 1.02 mmol). The mixture was allowed to warm to room temperature slowly, then poured into aqueous HCl and extracted with ether. The extracts were washed with water, saturated aqueous NaCl, and dried (Na2SO4). The solvent was removed under vacuum and the residue heated at reflux in 25% aqueous HCl for 4 h. After cooling and diluting with water, the mixture was extracted with ether. The extracts were washed with water, saturated aqueous NaCl, and dried (MgSO4). The solvent was removed under vacuum and the residue purified by chromatography on silica gel (ether, then 0.5% acetic acid/ether) to give the crude acid lactone.

Diazomethane, generated from diazaid (227 mg, 1.06 mmol), 60% KOH (2 ml), carbitol (2 ml) and ether (2 ml), was bubbled in an ether saturated stream of nitrogen through a solution of the crude acid in 10% methanol/ether (5 ml) until excess diazomethane was observed, then acetic acid added to quench. The solvent was removed under vacuum and the residue purified by chromatography on silica gel (50–70% ether/petroleum ether 40°–60° C.) to give the title compound (185 mg, 52%) as an oil, comprising a 1:1 mixture of diastereoisomers.

(d) ±(3R*,5R*) 3-(Carboxymethyl)-5-[6-(2,4dichlorophenyl)hexyl]tetrahydrofuran-2-one and its diastereoisomer Aqueous NaOH (1M, 1.43 ml, 1.43 mmol) was added slowly to a stirred solution of the diastereoisomers of ±3-(carbomethoxymethyl)-5-[6-(2,4-dichlorophenyl)-hexyl]tetrahydrofuran-2-one (185 mg, 0. 478 mmol) in methanol (5 ml) at 0° C. After 5 min at 0° C., the mixture was stirred at room temperature for 6 h, then poured into aqueous HCl and extracted with ether. The solvent was removed under vacuum and the residue heated at 60° C. in a 1:1 mixture of 3M aqueous HCl and tetrahydrofuran for 6 h. The mixture was cooled and extracted with ether. The extracts were washed with water, saturated aqueous NaCl, and dried (MgSO$_4$). The solvent was removed under vacuum to give an oil, which slowly crystallised. The solid was recrystallised (ether/petroleum ether 40°–60° C.) to give the title compound (126 mg, 71%), m.p. 57°–59° C.

$C_{18}H_{22}Cl_2O_4$ Found C 57.73%, H 5.81%. Requires C 57.92%, H 5.94%.

EXAMPLE 11

±(1'R*,3S*,5R*)
3-[Carboxy(hydroxy)methyl]-5-[6-(2,4-dichlorophenyl)hexyl]-3-hydroxytetrahydrofuran-2-one Employing the method of example 2, substituting ±(2R*,3S*,5R*) 3-carboxy-11-(2,4-dichlorophenyl)-2,3,5-trihydroxyundecanoic acid, disodium salt for ±(3R*,5S*) 3-carboxy-11-(2,4-dichlorophenyl)-3,5-dihydroxyundecanoic acid, disodium salt, gave the title compound.

$C_{18}H_{22}Cl_2O_6$ Found C 53.16% H 5.35% Requires C 53.35% H 5.47%.

EXAMPLE 12

±(3R*,5S*)
5-{6-[2,4-Bis(trifluoromethyl)phenyl]hexyl}-3-carboxymethyl-3-hydroxytetrahydrofuran-2-one (a) 2,4-Bis(trifluoromethyl)benzyltriphenylphosphonium Bromide N-Bromosuccinimide (3.17 g, 17.8 mmol) was added in portions to a stirred solution of 2,4-bis(trifluoromethyl)benzyl alcohol (3.96 g, 16.2 mmol) and triphenylphosphine (4.68 g, 7.8 mmol) in dichloromethane (40 ml) at 0° under argon, and the solution stirred at room temperature for 90 h. The solvent was removed under reduced pressure, and the residue loaded on to a pad of silica gel. The product was eluted with 50% ether/petroleum ether 40°–60° C.

A solution of the crude bromide and triphenylphosphine (4.25 g, 16.2 mmol) in toluene (35 ml) was heated under reflux for 3 h, then cooled. The solid was filtered off, washed with ether, and dried to give the title compound (7.23 g, 78%) as a solid, m.p. 239°–244° C.

(b) ±5-(Carbomethoxymethyl)-3-(5-hydroxypentyl)-5-methoxycarbonyl-4,5-dihydroisoxazole A solution of di-isobutylaluminium hydride in dichloromethane (1.0M, 125 ml, 125 mmol) was injected over 15 min into a stirred solution of ε-caprolactone (13.0 g, 114 mmol) in dichloromethane (100 ml) at −78° under argon. The solution was stirred for 20 min, then the cold bath removed, and water (41 ml, 2.28 mol) injected. The mixture was stirred vigorously while allowing to warm to room temperature. When the solid had separated, ethyl acetate was added, followed by excess sodium bicarbonate, and stirring was continued for 10 min. The solids were filtered off through a pad of hyflo, and the solvent removed from the filtrate under reduced pressure.

Aqueous Na$_2$CO$_3$ (2M, 100 ml, 200 mmol) was added slowly with vigorous stirring to a mixture of the crude hydroxyaldehyde and hydroxylamine hydrochloride (25.3 g, 364 mmol) in ether (200 ml). The mixture was stirred for 3 h after the addition, then NaCl added to saturate the aqueous layer. The ether layer was separated, and the solvent removed under reduced pressure. The aqueous layer was extracted with isobutanol.

The organic extracts were combined with the residue from the initial extract, washed with saturated aqueous NaCl, and dried (MgSO$_4$). The solvent was removed under reduced pressure, and traces of isobutanol removed by azeotropic distillation with toluene.

Aqueous sodium hypochlorite (~15%, 175 ml, ~350 mmol) was added dropwise to a stirred solution of the crude oximes, dimethyl itaconate (22.1 g, 140 mmol) and triethylamine (1 ml, 7.17 mmol) in dichloromethane (100 ml) cooled in a water bath. The mixture was stirred for 1 h, then filtered through hyflo. The organic layer was separated, and the aqueous extracted with dichloromethane. The extracts were washed with water, saturated aqueous NaCl, and dried (MgSO$_4$), then the solvent removed under reduced pressure. Column chromatography of the residual oil on silica gel (50–100% ether/petroleum ether 40°–60° C., then ethyl acetate) gave the title compound (23.1 g, 69%) as an oil.

(c) ±3-{6-[2,4-Bis(trifluoromethyl)phenyl]-5-hexenyl}-5-(carbomethoxymethyl)-5-methoxycarbonyl-4,5-dihydroisoxazole Dimethylsulphoxide (0,692 ml, 9.74 mmol) was injected dropwise into a stirred solution of oxalyl chloride (0,425 ml, 4.87 mmol) in dichloromethane (10 ml) at −78° under argon. After 2 min, a solution of ±5-(carbomethoxymethyl)-3-(5 -hydroxypentyl)-5-methoxycarbonyl-4,5-dihydroisoxazole (1.00 g, 3.48 mmol) in dichloromethane (5 ml) was added by cannula, and the mixture stirred for 30 min. Triethylamine (2.13 ml, 15.3 mmol) was injected, then the mixture allowed to warm to room temperature, poured into aqueous HCl, and extracted with dichloromethane. The extracts were washed with water, saturated aqueous NaCl, and dried (MgSO$_4$). The solvent was removed under reduced pressure, and the crude aldehyde dried by evaporation of a toluene solution. Sodium hydride (60% oil suspension, 146 mg, 3.65 mmol) was washed with petroleum ether 40°–60° under argon, then heated with dimethylsulphoxide (5 ml) at 70–90° until all solid had dissolved. After cooling in a water bath, a solution of 2,4-bis(trifluoromethyl)benzyltriphenylphosphonium bromide (1.98 g, 3.48 mmol) in dimethylsulphoxide (15 ml) was added by cannula, and the mixture stirred at room temperature for 15 min. A solution of the crude aldehyde in dimethylsulphoxide (5 ml) was added, the mixture stirred for 20 h, then poured into aqueous HCl and extracted with ether. The extracts were washed with water, saturated aqueous NaCl, and dried (MgSO$_4$). The solvent was removed under reduced pressure, and the residue purified by chromatography on silica gel (50–70% ether/petroleum ether 40°–60° ) to give the title compound (0.56 g, 33%) as a mixture of E and Z isomers.

(d) ±Methyl 11-[2,4-Bis(trifluoromethyl)phenyl]-3-hydroxy3-methoxycarbonyl-5-oxo-undecanoate.

A solution of ±3-{6-[2,4-bis(trifluoromethyl)phenyl]-5-hexenyl}-5-(carbomethoxymethyl)-5-methoxycarbonyl-4,5-dihydroisoxazole (659 mg, 1.33 mmol) and boric acid (247 mg, 3.99 mmol) in methanol/water (10:1, 10 ml) was shaken with Raney nickel (~300 mg) under hydrogen at 40 psi for 4 h. The hydrogen was replaced with nitrogen, then the catalyst filtered off through hyflo. The filtrate was diluted with water, and extracted with ethyl acetate. The extracts were washed with water, saturated aqueous NaCl, and dried (MgSO$_4$). The solvent was removed under reduced pressure.

A solution of the crude ketone in methanol (10 ml) was shaken with platinum oxide (36 mg, 0.159 mmol) under hydrogen at 50 psi for 8 h, then the hydrogen replaced with nitrogen and the catalyst filtered off through hyflo. The solvent was removed under reduced pressure and the residue columned on silica gel (50–80% ether/petroleum ether 40°-60°) to give the title compound (543 mg, 82%) as an oil.

(e) ±(3R*,5S*) 5-{6-[2,4-Bis(trifluoromethyl)phenyl]-hexyl}-3-carboxymethyl-3-hydroxytetrahydrofuran-2-one Following the procedures described in examples 1 (g) and 2, substituting ±methyl 11-[2,4-Bis (trifluoromethyl)phenyl]-3-hydroxy-3-methoxycarbonyl-5-oxo-undecanoate for ± methyl 11(2,4-dichlorophenyl)-3-hydroxy-3-methoxycarbonyl-5-oxo-undecanoate, gave the title compound as a solid, m.p. 70°–73° C.

$C_{20}H_{22}F_6O_5$ Found C 52.50% H 4.82% Requires C 52.64% H 4.86%.

EXAMPLE 13

±(3R*,5S*) 3-Carboxy-11-(4-chloro-2-trifluoromethylphenyl)-3,5-dihydroxyundecanoic acid, disodium salt (a) ±5-Carbomethoxymethyl-3-hex-5-enyl-5-methoxycarbonyl4,5-dihydroisoxazole The Swern oxidation of ±5-(carbomethoxymethyl)-3-(5-hydroxypentyl)-5-methoxycarbonyl-4,5-dihydroisoxazole (1.00 g, 3.48 mmol) was carried out as described in example 12(c).

A solution of n-butyllithium in hexane (2.5M, 1.75 ml, 4.38 mmol) was added dropwise to a stirred suspension of methyltriphenylphosphonium bromide (1.4 9 g, 4.18 mmol) in tetrahydrofuran (19 ml) at 0° under argon. After 30 min, the solution was cooled to −78° C., and a solution of the crude aldehyde in tetrahydrofuran (6 ml) was added by cannula. The mixture was stirred 5 min at −78° C., 30 min at 0° C., then poured into aqueous HCl and extracted with ether. The extracts were washed with water, saturated aqueous NaCl, and dried (MgSO$_4$). The solvent was removed under reduced pressure, and the residue purified by column chromatography on silica gel (40–60% ether/petroleum ether 40°-60°) to give the title compound (570 mg, 58%) as an oil.

(b) ±5-Carbomethoxymethyl-3-[6-(4-chloro-2-trifluoromethylphenyl)-5-hexenyl]-5-methoxycarbonyl-4,5-dihydroisoxazole A solution of 5-chloro-2-iodobenzotrifluoride (613 mg, 2.00 mmol), ±5-carbomethoxymethyl-3-hex-5-enyl-5-methoxycarbonyl-4,5-dihydroisoxazole (567 mg, 2.00 mmol) and tributylamine (0.477 ml, 2.00 mmol) in N-methylpyrrolidinone (4 ml) was heated with palladium acetate (5 mg, 0.022 mmol) under argon in an oil bath at 110° C. for 18 h, then cooled, poured into aqueous HCl, and extracted with ether. The extracts were washed with water, saturated aqueous NaCl, and dried (MgSO$_4$). The solvent was removed under reduced pressure, and the residue purified by column chromatography on silica gel (50–80% ether/petroleum ether 40°-60°) to give the title compound (534 mg) contaminated with other isomeric olefins.

(c) ±(3R*,5S*) 3-Carboxy-11-(4-chloro-2-trifluoromethyl-phenyl)-3,5-dihydroxyundecanoic acid, disodium salt Following the procedures described in example 12(d) and (e), substituting ±5-carbomethoxymethyl-3-[6-(4-chloro-2-trifluoromethylphenyl)-5-hexenyl]-5-methoxycarbonyl-4,5dihydroisoxazole for ±3-{6-[2,4-bis(trifluoromethyl)phenyl]-5-hexenyl)-5-(carbomethoxymethyl)-5-methoxycarbonyl4,5-dihydroisoxazole, gave the title compound as a solid, m.p. >250° C.

$C_{19}H_{22}ClF_3Na_2O_6 \cdot 0.5H_2O$ Found C 46.02% H 4.77% Requires C 46.21% H 4.69%.

EXAMPLE 14

±(3R*,5S*) 11-(2-Acetyl-4-chlorophenyl)-3-carboxy-3,5-dihydroxyundecanoic acid, disodium salt (a) 5-Chloro-1-(1,1-ethylenedioxyethyl)-2-methylbenzene Acetyl chloride (8.43 ml, 118.5 mmol) was injected into a stirred mixture of aluminium trichloride (15.8 g, 118.5 mmol) and dichloromethane (50 ml) under argon. When the solid had dissolved, 4-chlorotoluene (4.67 ml, 39.5 mmol) was injected. The solution was stirred for 20 h, then poured on to ice. The mixture was partitioned between salted water and ether, and the organic extracts washed with water, saturated aqueous NaCl, and dried (MgSO$_4$). The solvent was removed under reduced pressure, and the residue purified by column chromatography on silica gel (5–15% ether/petroleum ether 40°-60°) to give a mixture (~57:43) of 2-acetyl and 3-acetyl-4-chlorotoluene.

A solution of the isomeric ketones, ethanediol (16.15 ml, 289 mmol), and p-toluenesulphonic acid monohydrate (550 mg, 2.89 mmol) in toluene (50 ml) was heated at reflux for 2 h, using a Dean and Stark separator to remove water. The solution was cooled, poured into water, and extracted with ether. The extracts were washed with water, saturated aqueous NaCl, and dried (MgSO$_4$). The solvent was removed under reduced pressure, and the residue purified by column chromatography on silica gel (2–8% ether/petroleum ether 40°-60°) to give the title compound (2.98 g, 35%) as an oil.

(b) 4-Chloro-2-(1,1-ethylenedioxyethyl)benzyltriphenylphosphonium Bromide

A solution of 5-chloro-l-(1,1-ethylenedioxyethyl)-2-methylbenzene (2.97 g, 14.0 mmol) and N-bromosuccinimide (2.74 g, 15.4 mmol) in carbon tetrachloride (30 ml) was heated at reflux for 3 h, then cooled. The solvent was removed under reduced pressure, and the residue triturated with 20% ether/petroleum ether 40°-60° C. The extracts were filtered through a pad of silica gel, and the solvent removed from the filtrate under reduced pressure. The residue was purified by column chromatography on silica gel (3–9% ether/petroleum ether 40°-60° C.).

A solution of the bromide and triphenylphosphine (3.84 g, 14.7 mmol) in toluene (30 ml) was heated at reflux for 3 h, then cooled. The solid was filtered off, washed with ether, and dried under reduced pressure to give the title compound (5.94 g, 77%), m.p. 204°–209° C.

(c) ±Methyl 11-[4-Chloro-2-(1,1-ethylenedioxy)-phenyl]-3-hydroxy-3-methoxycarbonyl-5-oxo-undecanote Following the procedures described in example 12(c) and (d), substituting 4-chloro-2-(1,1-ethylenedioxyethyl)benzyltriphenylphosphonium bromide for 2,4-bis(-trifluoromethyl)benzyltriphenylphosphonium bromide, gave the title compound as an oil.

(d) ±(3R*,5S*) 11-(2-Acetyl-4-chlorophenyl)-3-carboxy-3,5-dihydroxyundecanoic acid, disodium salt Sodium borohydride (155 mg, 4.10 mmol) was added slowly in portions to stirred acetic acid (6 ml) cooled in a cold water bath. The solution was stirred for 5 min, then a solution of ± methyl 11-[4-chloro-2-(1,1-ethylenedioxy)phenyl]-3-hydroxy-3-methoxycarbonyl-5-oxo-undecanoate (510 mg, 1.05 mmol) in acetic acid (3 ml) was added. The mixture was stirred at room temperature for 1 h, then poured into salted water and extracted with ether. The extracts were washed with water, saturated aqueous NaCl, and dried (MgSO$_4$). The solvent was removed under reduced pressure.

A solution of the crude reduced product in trifluoroacetic acid/water (10:1, 10 ml) was stirred at room temperature for 1.5 h, then diluted with water and extracted with ether. The extracts were washed with water, saturated aqueous NaCl, and dried (MgSO$_4$). The solvent and excess trifluoroacetic acid were removed under reduced pressure.

Aqueous NaOH (1M, 3.15 ml, 3.15 mmol) was added dropwise to a stirred solution of the crude ketone in ethanol (20 ml) at 0° C. The mixture was allowed to warm to room temperature, then stirred for 18 h. Ethanol (20 ml) was added, and the solid filtered off. Recrystallisation from aqueous ethanol gave the title compound (337 mg, 70%) as a solid, m.p. >250° C.

$C_{20}H_{25}ClNa_2O_7$ Found C 52.01% H 5.65% Requires C 52.35% H 5.49%.

EXAMPLES 15 and 16

Following the procedures described in example 14, substituting the appropriate acid chloride for acetyl chloride, gave the following compounds:

EXAMPLE 15

±(3R*,5S*)
11-(2-Benzoyl-4-chlorophenyl)-3-carboxy-3,5-dihydroxyundecanoic acid, disodium salt (0.3H$_2$O)

$C_{25}H_{27}ClO_7Na_2.0.32H_2O$ Found C 57.01% H 5.29% Requires C 57.01% H 5.29%.

EXAMPLE 16

±(3R*,5S*)
11-(2-Butanoyl-4-chlorophenyl)-3-carboxy-3,5-dihydroxyundecanoic acid, disodium salt $C_{22}H_{29}ClNa_2O_7.0.33H_2O$ Found C 53.61% H 6.10% Requires C 53.61% H 6.07%.

EXAMPLES 17–20

Resolution of Compounds of Examples 1 and 2

EXAMPLE 17

(+) (3R*,5S*)
3-Carboxymethyl-5-[6-(2,4-dichlorophenyl)-hexyl]-3-hydroxytetrahydrofuran-2-one The lactone of example 2 (3.4 g, 8.9 mmol) was dissolved in ethanol-water (96:4) (20 ml). To this was added a solution of D-(−)-threo-2-amino-1-(4-nitrophenyl)propan-1, 3-diol (1.89 g, 8.9 mmol) in the same solvent (70 ml). After 3 hr, the crystallised solid (1.42 g) was collected and dried in vacuo. This salt was suspended in water and 2M HCl added to pH 1–2. This was extracted with ether (3×), the combined extracts washed with water (1×) and dried over MgSO$_4$. Concentration gave a white solid (0.9 g) which was recrystallised from CHCl$_3$/hexane to give the pure (+)-enantiomer of example 2 (0.57 g); mp 80°–80.5° C.; $[\alpha]D^{25} = +19.4$ (c=0.5% w/v; EtOH).

$C_{18}H_{22}Cl_2O_5$ Found C 55.54% H 5.61% Requires C 55.54% H 5.70%

EXAMPLE 18

(+) (3R*,5S*)
3-Carboxy-11-(2,4-dichlorophenyl)-3,5-dihydroxyundecanoic acid, disodium salt The compound of example 17 (160 mg) was dissolved in ethanol (2.5 ml) and 5% aqueous NaOH solution (0.64 ml) in water (1.86 ml) added with stirring. After ca 10 min, the precipitated solid was collected, washed with 1:1EtOH-H$_2$O and recrystallised from water-ethanol to give the (+)-enantiomer of example 1 (100 mg), $[\alpha]D^{25} = +23.3$ (c=0.16% w/v; H$_2$O).

$C_{18}H_{22}Cl_2O_6Na_2.H_2O$ Found C 45.84% H 4.91% Requires C 46.07% H 5.15%

EXAMPLE 19

(−) (3R*,5S*)
3-Carboxymethyl-5-[6-(2,4-dichlorophenyl)-hexyl]-3-hydroxytetrahydrofuran-2-one By an analogous procedure to example 17, employing the enantiomeric amine, (L-(+)-threo-2-amino-1-(4-nitrophenyl)propan-1,3-diol), gave the pure (−)-enantiomer of example 2, $[\alpha]D^{25} = -19.5$ (c=0.5% w/v; EtOH).

$C_{18}H_{22}Cl_2O_5$ Found C 55.37% H 5.58% Requires C 55.54% H 5.70%

EXAMPLE 20

(−) (3R*,5S*) 3-Carboxy-11-(2 4-dichlorophenyl)-3 5-dihydroxyundecanoic acid, disodium salt Substituting the compound of example 19 (100 mg) in the procedure of example 18 gave the (−)-enantiomer of example 1 (65 mg), $[\alpha]D^{25} = -20.6$ (c=0.1% w/v; H$_2$O).

$C_{18}H_{22}Cl_2O_6Na_2.H_2O$ Found C 45.69% H 4.98% Requires C 46.07% H 5.15%

Data:
1. RAT ATP CITRATE LYASE (ACL) ASSAY
Purification of ATP Citrate lyase-human and rat enzymes
(i) rat enzyme
Male Wistar rats were fasted for 24 h, then fed on a high carbohydrate diet for 72 h prior to removal of the livers. ATP Citrate lyase was prepared according to the method of Wraight et al (Anal. Biochem., 1985, 144, 604-609) with modifications for large scale purification according to Wells (Eur. J. Biochem., 1991, 199, 163-168). Protein obtained by this method was pure as judged by SDS-PAGE.

(ii) human enzyme

Human ATP citrate lyase was prepared as described in European Journal of Biochemistry, 1992, 204, 491-99, with modifications for large scale purification according to Wells as referred to above. Protein obtained by this method was pure as judged by SDS-PAGE.

Assay of ATP Citrate lyase in the presence of inhibitors

ATP Citrate lyase activity was assayed at 25° C. by reducing the oxaloacetate produced with malate dehydrogenase and NADH while monitoring at 340 nm using a Beckman DU50 spectrophotometer (according to the method of Linnet al (J. Biol. Chem., 1979, 254, 1691-1698)). Briefly, ATP citrate lyase (human or rat) was added to a 1 ml cuvette containing 50 mM Tris/HCl, pH=8.0, 0.2 mM NADH, 10 mM $MgCl_2$, 10 mM KCl, 5 mM ATP, 200 μM coenzyme A, 10 mM dithiothreitol and malate dehydrogenase. An aqueous solution of inhibitor was added (for inhibitors which were insoluble in water, a stock solution was prepared in DMSO. However the final DMSO concentration in the cuvette was not allowed to exceed 1%.). Finally, tripotassium citrate was added to 100 μM final. This is $K_m$ for citrate (Wells et al (Eur. J. Biochem., 1992, 204, 249-255) and Houston et al (Biochim. Biophys. Acta, 1985, 844, 233-239)). Data analysis was performed using the curve fitting package Enzfitter (Elsevier Biosoft). For competitive inhibitors data was fitted to the equation $$v = v_{max}/(2 + I/K_i)$$

where v is the observed rate and I is the concentration of inhibitor added. Thus the dissociation constant $K_i$ for the inhibitor could be found.

Results:

The compound of Example 1 had a Ki of 0.8 μM (rat); and the compound of Example 2 (lactone of Example 1) was inactive (rat).

The compounds of Examples 3 to 9 had Ki values (rat) of less than 30 μM.

The compounds of Examples 13 to 16 had Ki values (human) of less than 82 μM.

The compounds of Example 18 had a Ki value of 0.76 μM (human) and 0.70 μM (rat); and the compound of Example 20, a Ki value of 0.69 μM (human) and 0.70 μM (rat).

2. Measurement of effect of compounds on cholesterol (CL) and fatty acid (FA) synthesis in HepG2 Cells HepG2 cells were cultured in 24-well cell culture plates in DMEM (Dulbecco's Modified Eagle's Medium) containing Hepes (20 mM), bicarbonate (10 mM), glutamine (2 mM) and foetal calf serum (10% w/v). Once the cells had grown to between 80% and 90% confluence, the medium was replaced by DMEM without the addition of foetal calf serum and the cells incubated overnight. The rates of cholesterol and fatty acid synthesis were then measured by the addition of $^3H_2O$, to a specific radioactivity of 71 mCi/mmol, for the final 90 min of the incubation. Vehicle or test compound were added to the medium either 1.5 or 14.5 hr prior to the addition of $^3H_2O$ to give the final desired concentration. Incubations were terminated and the rates of cholesterol and fatty acid synthesis determined from the amounts of $^3H$ incorporated into cellular cholesterol and fatty acids as described previously (Berkhout et al.; Biochem J., 1990, 272, 181).

Results

| | Conc. (μM) | CL synthesis % of control | FA synthesis % of control |
|---|---|---|---|
| Compound of Example 1 | 1000 | 80 ± 6 | 123 ± 3 |
| Compound of Example 2 (lactone of Example 1) | 30 | 8 ± 3 | 32 ± 3 |
| Compound of Example 11 | 3 | 69 ± 13 | 74 ± 11 |
| Compound of Example 11 | 10 | 86 ± 29 | 76 ± 13 |

3. Measurement of hyperlipidaemic activity in rats and dogs (a) Spmgue Dawley Rat The compound of example 2 was administered to Spmgue Dawley rats in their diet at a concentration of 0.125% (w:w) for 7 days. Measurement of plasma cholesterol levels and triglyceride levels by standard techniques indicated that the compound had reduced plasma cholesterol levels by 30% and plasma triglyceride levels by 64%.

25 (b) Dog The compound of example 2 was administered to male Beagle dogs at a level of 25 mg/kg/day for 2 weeks. Measurement of plasma cholesterol levels and triglyceride levels by standard techniques indicated that the compound had reduced plasma cholesterol levels by 20-25% and plasma triglyceride levels by 20-25%.

We claim:

1. A compound of structure (I):

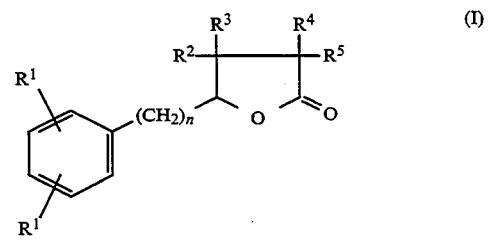

in which, each group $R^1$ is independently a lipophilic and/or electron withdrawing group; n is 5 to 8; and either $R^2$ and $R^3$ are both hydrogen, $R^4$ is hydrogen or hydroxy and $R^5$ is $CH(R^6)R^7$ in which $R^6$ is hydrogen or hydroxy and $R^7$ is a carboxyl group or a carboxylic acid ester group hydrolysable to a carboxyl group; or $R^4$ is hydrogen and $R^5$ is hydrogen or hydroxy, $R^2$ is hydroxy and $R^3$ is a carboxyl group or a carboxylic acid ester group hydrolysable to a carboxyl group; or $R^2$ and $R^3$ are hydrogen and $R^4$ and $R^5$ together form a group $=C(R^6)R^7$ in which $R^6$ and $R^7$ are as defined above, or a salt thereof.

2. A compound according to claim 1 in which $R^2$ and $R^3$ are both hydrogen, $R^4$ is hydroxy and $R^5$ is $CH(R^6)CO_2H$ in which $R^6$ is hydrogen.

3. A compound according to claim 1 in which $R^4$ is hydrogen, $R^5$ is hydrogen or hydroxy, $R^2$ is hydroxy and $R^3$ is $CO_2H$.

4. A compound of structure (IB):

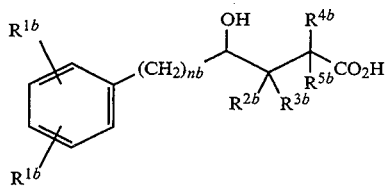

(IB)

in which
each group $R^{1b}$ is independently a lipophilic and/or electron withdrawing group; $n^b$ is 5 to 8; and
either $R^{2b}$ and $R^{3b}$ are both hydrogen, $R^{4b}$ is hydrogen or hydroxy and $R^{5b}$ is $CH(R^{6b})CO_2H$ in which $R^{6b}$ is hydrogen or hydroxy; or $R^{4b}$ is hydrogen and $R^{5b}$ is hydrogen or hydroxy, $R^{2b}$ is hydroxy and $R^{3b}$ is $CO_2H$; or $R^{2b}$ and $R^{3b}$ are hydrogen and $R^{4b}$ and $R^{5b}$ together form a group $=C(R^{6b})CO_2H$, or a pharmaceutically acceptable salt thereof.

5. A compound according to claim 4 in which $R^{2b}$ and $R^{3b}$ are both hydrogen, $R^{4b}$ is hydroxy, $R^{5b}$ is $(CHR^{6b})CO_2H$ in which $R^{6b}$ is hydrogen.

6. A compound of claim 1 that is:
±(3R*,5S*)3-carboxymethyl-5-[6-(2,4-dichlorophenyl)hexyl]-3-hydroxytetrahydrofuran-2-one,
±(4R*,5S*)4-carboxy-5-[8-(2,4-dichlorophenyl)octyl]-4-hydroxytetrahydrofuran-2-one,
±(4R*,5R*)4-carboxy-5-[8-(2,4-dichlorophenyl)octyl]-4-hydroxytetrahydrofuran-2-one,
±(3R*,5R*)3-(carboxymethyl)-5-[6-(2,4-dichlorophenyl)-hexyl]tetrahydrofuran-2-one,
(+)(3R*,5S*)3-carboxymethyl-5-[6-(2,4-dichlorophenyl)-hexyl]-3-hydroxytetrahydrofuran-2-one or
(−)(3R*,5S*)3-carboxymethyl-5-[6-(2,4-dichlorophenyl)-hexyl]-3-hydroxytetrahydrofuran-2-one.

7. A compound of claim 4 that is:
±(3R*,5S*)3-carboxy-11-(2,4-dichlorophenyl)-3,5-dihydroxyundecanoic acid, disodium salt,
(+)(3R*,5S*)3-carboxy-11-(2,4-dichlorophenyl)-3,5-dihydroxyundecanoic acid, disodium salt,
(+)(3R*,5S*)3-carboxy-11-(2,4-dichlorophenyl)-3,5-dihydroxyundecanoic acid, disodium salt,
±(E)-3-carboxy-11-(2,4-dichlorophenyl)-5-hydroxy-2-undecenoic acid,
±(2R*,3R*,5S*)3-carboxy-11-(2,4-dichlorophenyl)-2,3,5-trihydroxyundecanoic acid, disodium salt,
±(2R*,3S*,5R*)3-carboxy-11-(2,4-dichlorophenyl)-2,3,5-trihydroxyundecanoic acid, disodium salt, or
±(3R*,5S*)3-carboxy-11-(4-chloro-2-trifluoromethylphenyl)-3,5-dihydroxyundecanoic acid, disodium salt.

8. A pharmaceutical composition comprising a compound of structure (I) as defined in claim 1, in association with a pharmaceutically acceptable carrier.

9. A method of lowering serum triglyceride and cholesterol levels which comprises administering to a mammal in need thereof an effective amount of a compound of structure (I) as defined in claim 1.

10. A method of lowering serum triglyceride and cholesterol levels which comprises administering to a mammal in need thereof an effective amount of a compound of structure (IB) as defined in claim 4, or a pharmaceutically acceptable salt thereof.

* * * * *